United States Patent [19]

Light et al.

[11] 4,208,297

[45] Jun. 17, 1980

[54] USE OF NOVEL OXYHYDROCARBYLNORBORNANE DERIVATIVES FOR AUGMENTING OR ENHANCING THE AROMA OF DETERGENTS

[75] Inventors: Kenneth K. Light, Highlands; James M. Sanders, Eatontown; Manfred H. Vock, Locust, all of N.J.; Edward J. Shuster, Brooklyn, N.Y.; Joaquin Vinals, Red Bank, N.J.; William L. Schreiber, Jackson, N.J.; John B. Hall, Rumson, N.J.; Denis E. Hruza, Sr., Bricktown, N.J.; Venkatesh Kamath, Red Bank, N.J.; Braja D. Mookherjee, Holmdel, N.J.; Ching Y. Tseng, Middletown, N.J.; Mark A. Sprecker, Sea Bright, N.J.

[73] Assignee: International Flavors & Fragrances Inc., New York, N.Y.

[21] Appl. No.: 32,900

[22] Filed: Apr. 24, 1979

Related U.S. Application Data

[60] Division of Ser. No. 860,124, Dec. 13, 1977, Pat. No. 4,186,150, which is a continuation-in-part of Ser. No. 765,847, Feb. 4, 1977, Pat. No. 4,076,853.

[51] Int. Cl.² .......................... C11D 9/44; C11D 3/50
[52] U.S. Cl. .............................. 252/174.11; 252/108; 252/522 R
[58] Field of Search .................. 252/174.11, 522, 108; 260/586.6

[56] References Cited

U.S. PATENT DOCUMENTS 4,153,568  5/1979  Light et al. .................... 252/174.11

Primary Examiner—Mayer Weinblatt
Attorney, Agent, or Firm—Arthur L. Liberman; Franklin D. Wolffe

[57] ABSTRACT

Described is a process for augmenting or enhancing the aroma of a solid or liquid anionic, cationic or nonionic detergent comprising the step of intimately admixing with a solid or liquid cationic, anionic or nonionic detergent base and aroma augmenting or enhancing quantity of at least oxyhydrocarbylnorbornane having the structure:

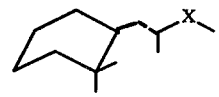

wherein X is carbonyl or carbinyl having the structures, respectively:

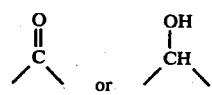

and wherein at least one of the dashed lines is a carbon-carbon single bond and the other of the dashed lines is a carbon-carbon single bond or a carbon-carbon double bond.

5 Claims, 6 Drawing Figures

IR SPECTRUM FOR EXAMPLE IB

IR SPECTRUM FOR EXAMPLE IC

USE OF NOVEL OXYHYDROCARBYLNORBORNANE DERIVATIVES FOR AUGMENTING OR ENHANCING THE AROMA OF DETERGENTS

This application is a divisional for application for U.S. Letters Patent, Ser. No. 860,124, filed on Dec. 13, 1977, now U.S. Pat. No. 4,186,150, issued on 1-29-80, which in turn is a continuation-in-part of application for U.S. Letters Patent, Ser. No. 765,847, filed on Feb. 4, 1977, now U.S. Pat. No. 4,076,853, issued on Feb. 28, 1978.

BACKGROUND OF THE INVENTION

The present invention relates to oxyhydrocarbylnorbornanes and compositions using said oxyhydrocarbylnorbornanes which have the generic structure:

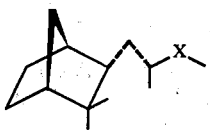

wherein at least one of the dashed lines is a carbon-carbon single bond and the other of the dashed line is a carbon-carbon single bond or a carbon-carbon double bond and X is carbonyl having the structure:

or carbinyl having the structure:

to augment or enhance the aroma of perfume compositions, perfumed articles and colognes or to impart aroma to such perfume compositions, perfumed articles or colognes.

There has been considerable work performed relating to substances which can be used to impart (modify, augment or enhance) fragrances to (or in) various consumable materials such as perfume compositions, colognes and perfumed articles including soaps, detergents, cosmetics and powders. These substances are used to diminish the use of natural materials, some of which may be in short supply and to provide more uniform properties in the finished product.

Natural, sweet pine, incense, camphene-like, sweet, green, floral, fruity, dried fruity, ionone-like, orris-like and nasturtium-like aromas dried, woody, piney, sweaty and geranic acid-like nuances are particularly desirable in several types of perfume compostions, perfumed articles and colognes.

U.S. Pat. No. 3,852,358 issued on Dec. 3, 1974 discloses a process for producing 2-acetyl-3,3-dimethyl-5-norbornene in both the exo and endo forms which have uses in perfumery and other fragrance applications. These compounds have the structures:

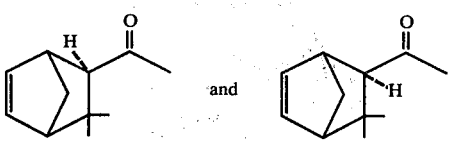

These compounds, produced by reaction of cyclopentadiene with mesityl oxide, are starting materials for producing a number of the compounds of our invention. However, the compounds of our invention have unexpected, unobvious and advantageous properties when compared with the 2-acetyl-3,3-dimethyl-5-norbornene of U.S. Pat. No. 3,852,358.

U.S. Pat. No. 3,942,761 discloses the use in perfumery of 4(2'-norbornyl)-2-butanones having the structure:

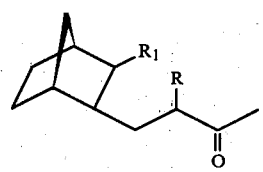

wherein $R_1$ is hydrogen or metyl and R is hydrogen or lower alkyl containing from 1 to 8 carbon atoms. Such compounds have structures which are different in kind from the structures of the compounds of our invention. Also disclosed as intermediates for producing the foregoing compounds are compounds having the generic structure:

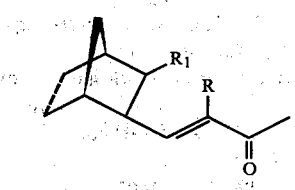

wherein the dotted line is a carbon-carbon single bond or a carbon-carbon double bond. In addtion, the following reaction sequence is set forth therein:

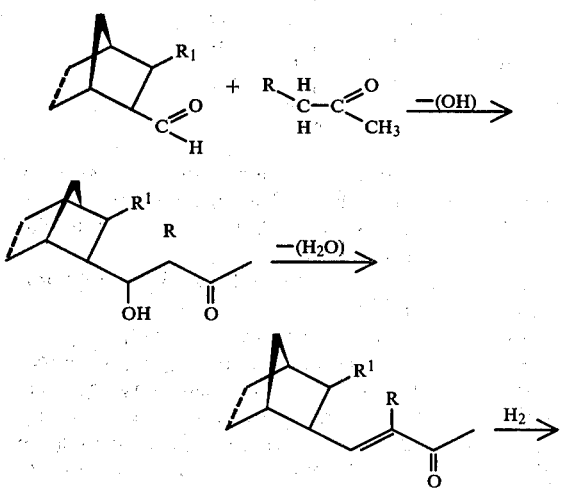

-continued

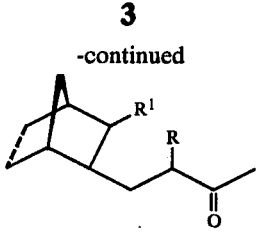

Arctander, "Perfume and Flavor Chemicals", 1969, Vol. 1, discloses the use in perform compositions and in foodstuff flavors of "fenchone", "fenchyl alcohol", "camphene carbinol", and "camphene carbinyl acetate", thus:

(i) "1385: FENCHONE
laevo-Fenchone. (dextro- is known but less common as a fragrance material).
1,3,3-Trimethyl-2-norbornanone.
1,3,3-Trimethyl bicyclo-1,2,2-heptanone-2.

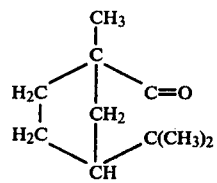

Warm-camphoraceous, powerful and diffusive, basically sweet odor.

Warm, somewhat burning and bitter taste with a medicinal note.

This ketone finds some use as a masking odor in industrial fragrances. It is also used in the reconstruction of Fennel oil and a few other essential oils.

In spite of its rather unpleasant taste, it is used in various Berry complex flavors, in Spice complexes and in certain types of Liquer flavoring.

The concentration used is about 0.1 to 5 ppm in the finished product."

(ii) "1387: FENCHYL ALCOHOL
1,3,3-Trimethyl-2-norbornanol
1,3,3-Trimethyl bicyclo-1,2,2-heptanol-2.
2-Fenchanol.
Fenchol.

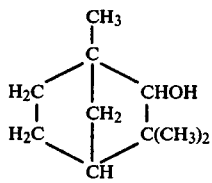

Powerful and diffusive, Camphor-like, but sweeter and more Citrus-like almost Lime-like odor with more or less of an earthy-dry character, according to the composition and isomer-ratio.

The taste is somewhat bitter-Lime-like, camphoraceous and slightly woody-musty.

This interesting alcohol (or mixed alcohols) finds use in perfume compositions ranging from woody or herbaceous to Citrus-Lime and even certain floral types. It produces power and "lift" to floral fragrances, and solid background to Lime and other Citrus bases, having the advantage over the Terpenes in being very stable in soap.

Fenchyl alcohol is also used in flavor compositions such as Strawberry and other berries, Lime and Spice, etc.

The concentration is normally low, e.g., 0.2 up to 5 ppm in the finished product."

(iii) "1028: 3,3-DIMETHYL-$\Delta^2$, beta-NORBORNANE-2-ETHANOL "Camphene carbinol".

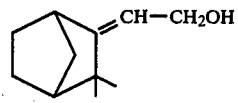

Sweet-camphoraceous, warm and soft odor with a woody undertone. Upon standing it may develop an odor resembling that of Celluloid.

Although rarely offered commerically, this chemical could find some use in perfume compositions of the woody, Oriental and orrisytype, in new variations of Pine fragrances, and in various soap and detergent perfumes."

(iv) "1029: 3,3-DIMETHYL-$\Delta^2$-beta-NORBORNANE-2-ETHYLACETATE "Camphene carbinyl acetate".

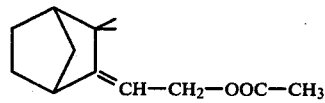

Mild and sweet-woody odor with a floral-piney undertone. The commercial products are probably not well-defined single chemicals, and great variations in odor have been observed.

This ester has been developed in line with the research on Sandalwood type odors. The parent alcohol "Camphene carbinol" was once considered useful as a Sandalwood type material, but it has found more use as a sweetening and enriching ingredient in sophisticated Pine fragrances. The title ester finds limited use in perfume compositions of woody character, Fougeres, Pine fragrances, etc. and it blends very well with the Cyclohexanol derivatives, Ionones, iso- Bornylacetate, Nitromusks, etc."

U.S. Patent 3,928,456 discloses monocyclic compounds having the generic structure:

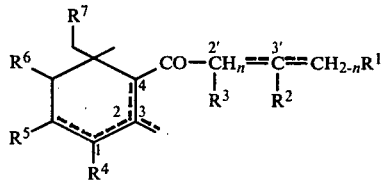

containing one double bond in position 2'- or 3'- of the acyl side-chain and either one double bond in position 1- or 2- (as shown in the above formula, the double bond in the 2 position can be either in the cycle or the side chain), or two conjugated double bonds in positions 1- and 3- of the cycle, the double bonds being represented by dotted lines, and wherein n is zero or 1, $R^1$, $R^2$ and $R^3$ represent hydrogen or one of them a lower alkyl radical, such as methyl or ethyl, and the others hydrogen, and $R^4$, $R^5$, $R^6$, and $R^7$ represent hydrogen or one of them a lower alkyl radical, such as methyl or ethyl, and the others hydrogen, as being useful in perfumery and food flavors and also flavors, beverages, animal feeds and tobaccos. Specifically disclosed in this patent is a compound having the structure:

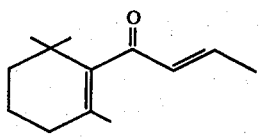

U.S. Application for Letters Patent Ser. No. 551,030, filed on Feb. 19, 1975 and now U.S. Pat. No. 4,000,050, discloses, interalia, perfumery uses of compounds having the structures:

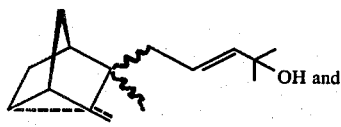

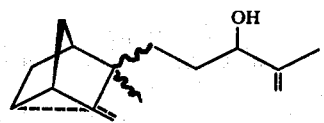

wherein one of the dashed lines is a carbon-carbon bond and each of the wavy lines is a carbon-carbon single bond, one of the carbon-carbon single bonds represented by the wavy line being epimeric with respect to the other of the carbon-carbon single bonds represented by the wavy line.

In addition, various processes and compounds relating to the synthesis of synthetic sandalwood oil components are described in the following U.S. Patents:

(i) Perfume Compounds and Process for Preparing Same—U.S. Pat. No. 3,673,261, issued June 27, 1972:
Compounds:

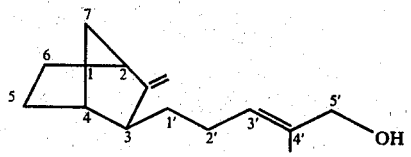

2-methylene-3-exo(trans-4'-methyl-5'-hydroxypent-3'-enyl)bicyclo[2.2.1]-heptane trans-3-Normethyl-β-santalol

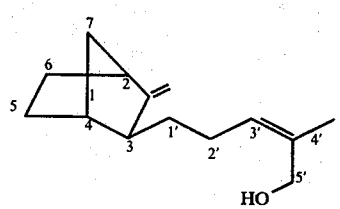

2-methylene-3-exo(cis-4'-methyl-5'-hydroxypent-3'-enyl)bicyclo[2.2.1]-heptane cis-3-normethyl-β-santalol

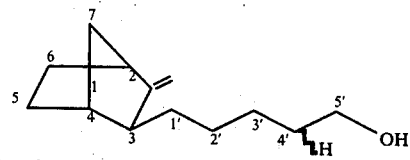

2-methylene-3-exo(4'-methyl-5'-hydroxypentyl)-bicyclo[2.2.1]heptane-3-normethyldihydro-β-santalol (ii) dihydro-β-santalol and Processes for Preparing Dihydro-β-santalol from 3-Endo-Methyl-3-Exo (4'-Methyl-5'-Hydroxyphenyl) Norcamphor—U.S. Pat. No. 3,673,263, issued June 27, 1972:

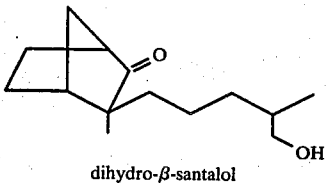

dihydro-β-santalol (iii) Process for Preparing β-Santalol from 3-Methyl-norcamphor—U.S. Pat. No. 3,662,008, issued May 9, 1972:

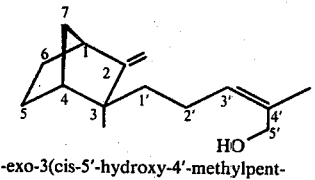

endo-3-methyl-exo-3(cis-5'-hydroxy-4'-methylpent-3'-enyl)-2-methylenebicyclo[2.2.1]heptane

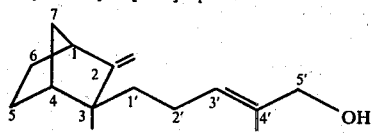

endo-3-methyl-exo-3(trans-5'-hydroxy-4'-methyl-pent-3'-enyl)-2-methylenebicyclo[2.2.1]heptane (iv) Process for Preparing Dihydro-β-Santalol from 3-Endo-methyl-3-Exo(4'-Methyl-5'-Hydroxypentyl) Norcamphor—U.S. Pat. No. 3,673,266, issued June 27, 1972:

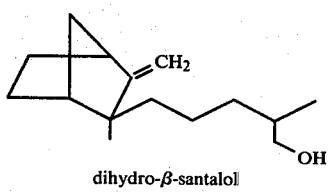

dihydro-β-santalol

None of the compounds disclosed in either U.S. Pat. No. 3,928,456 or U.S. Application for Letters Patent Ser. No. 551,030, filed Feb. 19, 1975 and now U.S. Pat. 4,000,050 have properties even closely similar to the properties of the "oxyhydrocarbylnorbornanes" of the instant application.

Chem Abstracts, Vol 84, 73728n (abstract of Karaev, et al, Zh. Org. Khim. 1975, 11(12), 2622) discloses preparation of the compound:

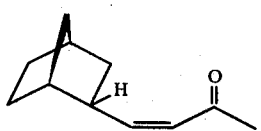

Klein and Rojahn, Chem. Abstracts, Vol. 84, 90327y (1976) discloses the use of compounds having the generic structure:

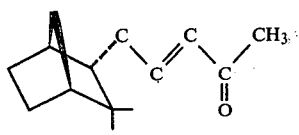

(wherein the dashed line is a single or double bond) as an intermediate in the preparation of β-santalol; but no organoleptic properties of these norbornane derivatives are disclosed.

U.S. Pat. No. 3,748,344, issued on July 24, 1973, discloses that chemical compounds characterized by the structural formula:

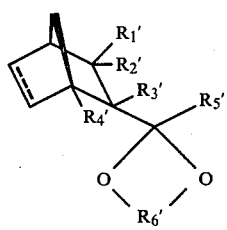

wherein the dashed line represents the presence of a single or a double bond wherein R$_1$', R$_2$', R$_3$' and R$_4$' each represent hydrogen or lower methyl and R$_5$' represents hydrogen or lower alkyl and R$_6$' represents a polymethylene radical of from 2 to 4 carbon atoms which is unsubstituted or substituted with lower alkyl, which "as a whole exhibits a characteristic, pleasant, strong and long lasting aroma which is highly useful in the preparation of fragrance compositions and perfume products". Various notes are described such as green, cuminic, walnut, raw potato, earthy, camphoraceous, civet, walnut bark, neroli, anise, vegetable, menthone, animal, minty, eucalyptol, cucumber, pine and fecal.

In addition, U.S. Pat. No. 3,748,344 discloses as chemical intermediates for preparing the above ketal, a compound having the generic structure:

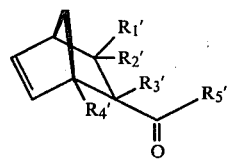

wherein R$_1$', R$_2$', R$_3$', R$_4$' and R$_5$' have the same meaning as defined above.

However, the specific compound of our invention is not set forth in U.S. Pat. No. 3,748,344.

No prediction of the organoleptic properties of the compound of the instant invention can be made by a study of the disclosure of U.S. Pat. No. 3,748,344.

Chemical Abstracts, Vol. 71, 49664z (abstract of Sadykh-Zade, et al (U.S.S.R.) Dokl. Akad. Nauk Azerb. SSR 1968, 24(11), 38–41) discloses the synthesis of exo and endo forms of the compounds having the structures:

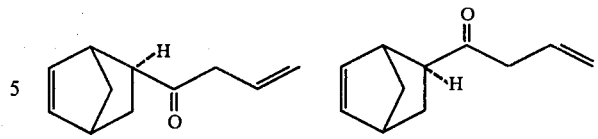

Chemical Abstracts, Vol. 81, 135512m (abstract of Akhmedov, I. M., et al (Inst. Georg. Fiz. Khim., Baku, U.S.S.R.) Dokl. Akad. Nauk Az. SSR 1974, 30(4), 18–21) discloses the synthesis of the compound having the structure:

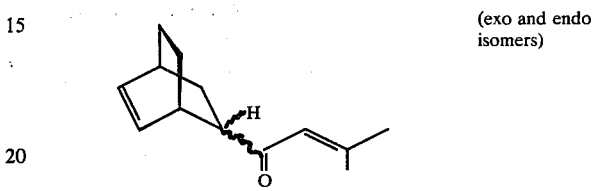

(exo and endo isomers)

None of the Chemical Abstract references discloses compounds which have a close structural relationship to the oxyhydrocarbylnorbornanes of the instant invention. In any event, the organoleptic properties of the compounds of the Chemical Abstract references are different in kind from those of the oxyhydrocarbylnorbornanes of the instant invention.

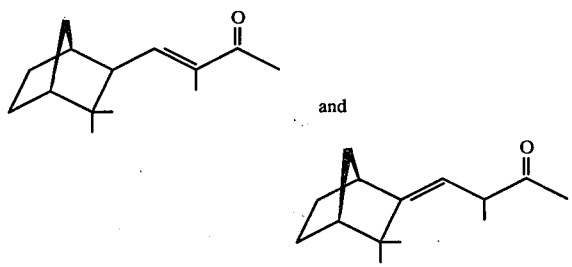

of our invention produced according to Example IA.

Figure 2:
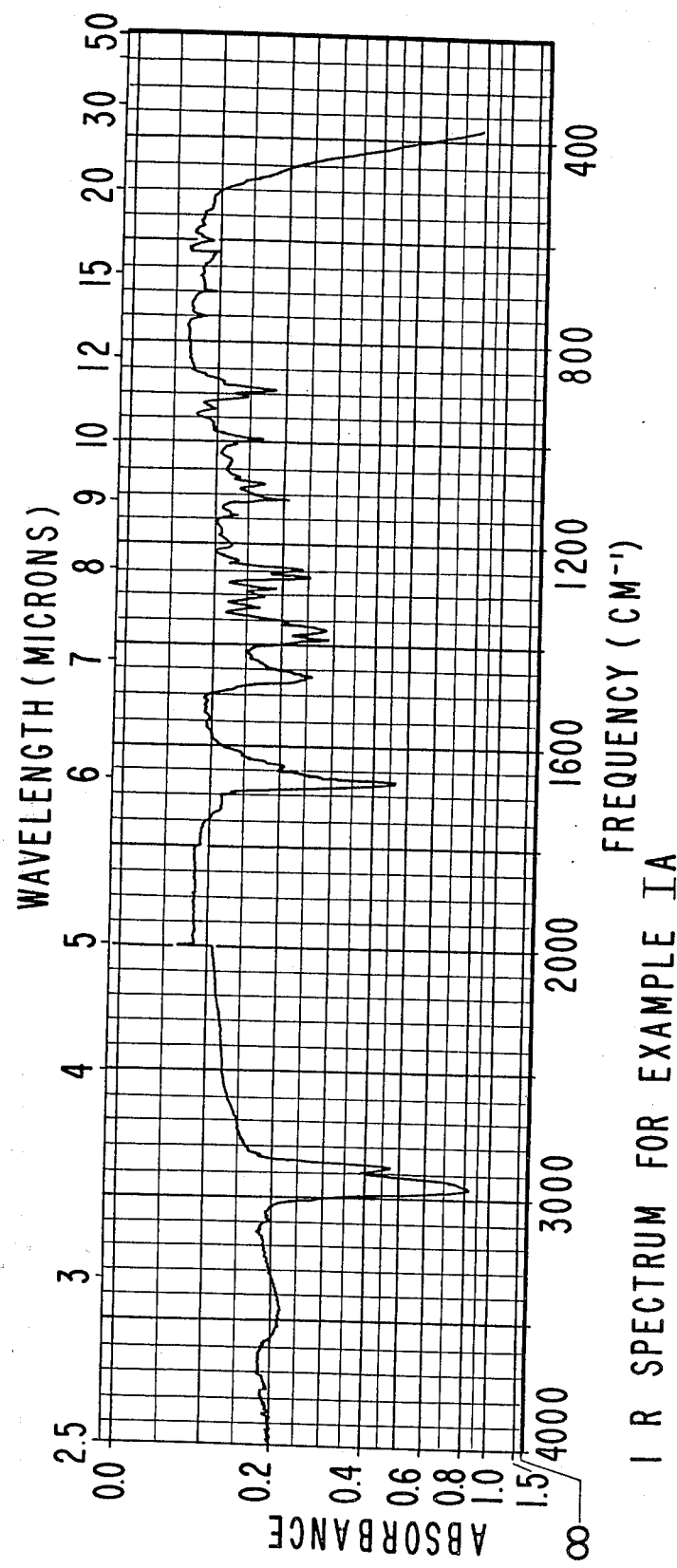

FIG. 2 is the Infrared spectrum for the mixture of oxyhydrocarbylnorbornanes, β,3,3-trimethyl-2-norbornyl-α-buten-γ-one and β,3,3-trimethyl-2-norbornylidenebutan-γ-one having the structures respectively:

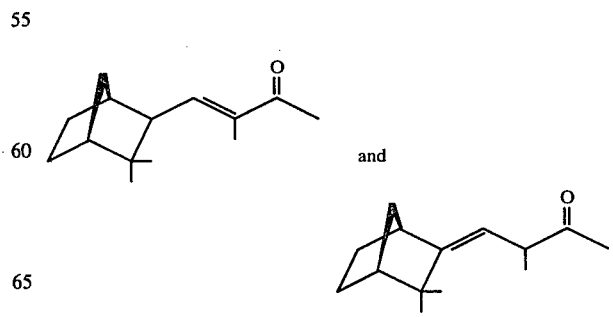

of our invention produced according to Example IA.

Figure 3:
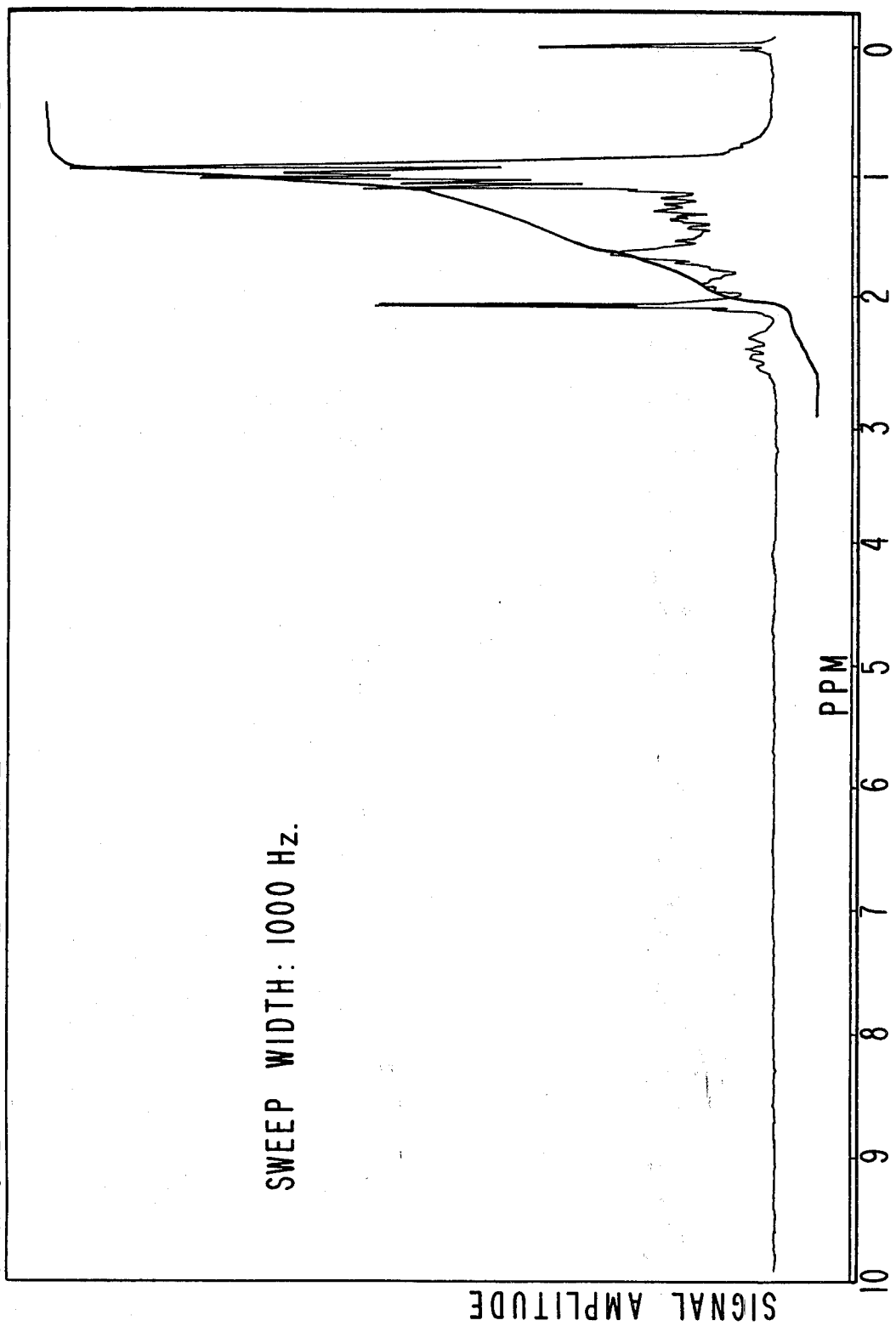

FIG. 3 is the NMR spectrum for the oxyhydrocarbyl-norbornane, 4-(3,3-dimethyl-2-norbornyl)-3-methyl-2-butanone having the structure:

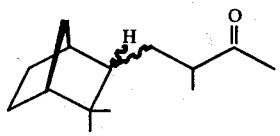

of our invention produced according to Example IB.

Figure 4:
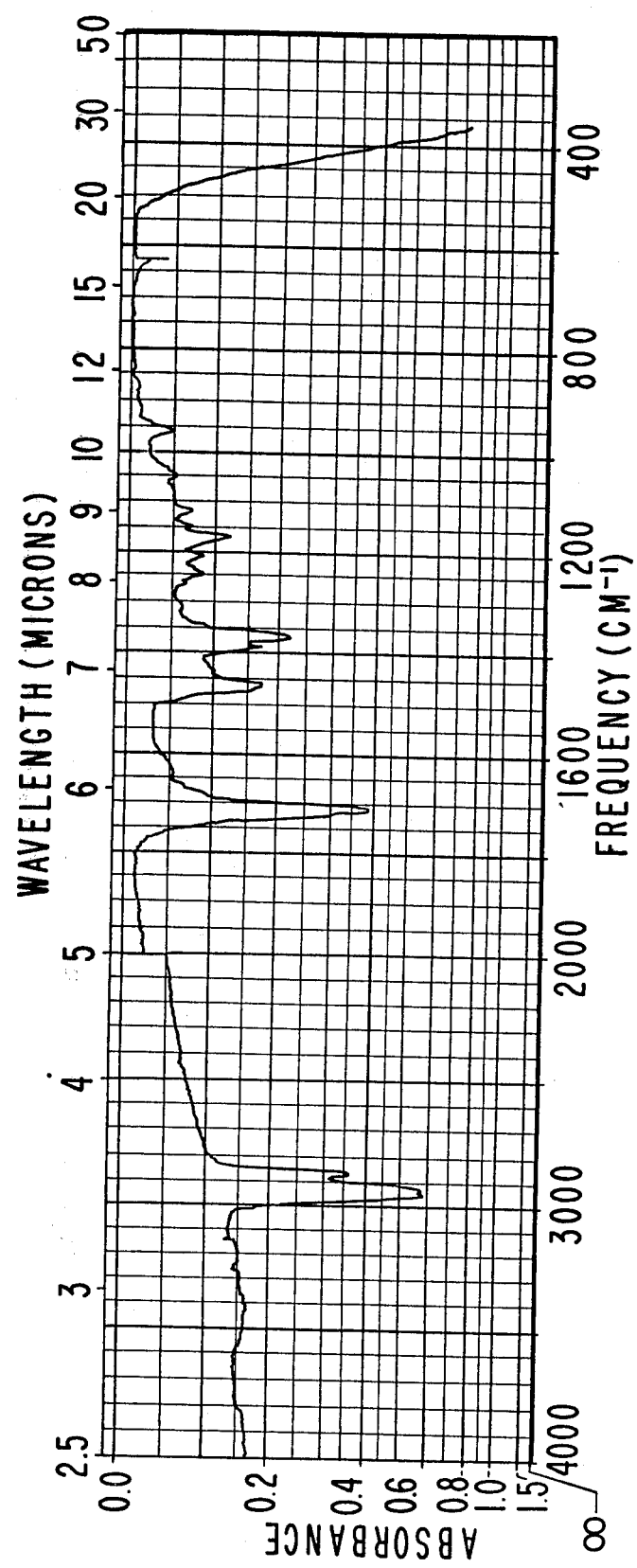

FIG. 4 is the Infrared spectrum for the oxyhydrocarbylnorbornane, 4-(3,3-dimethyl-2-norbornyl)-3-methyl-2-butanone having the structure:

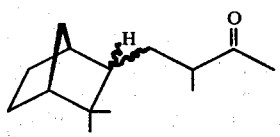

of our invention produced according to Example IB.

Figure 5:
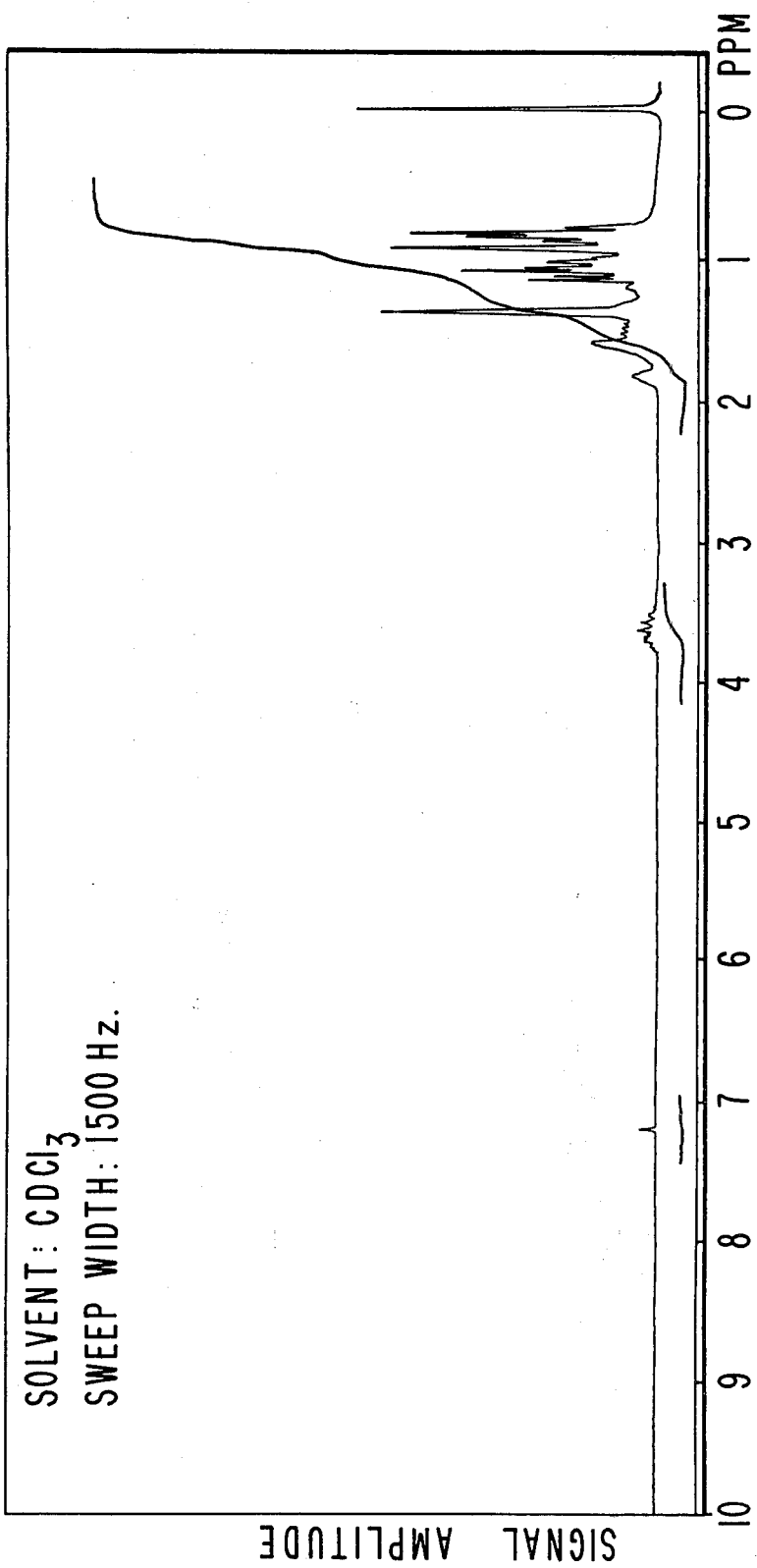

FIG. 5 is the NMR spectrum for the oxyhydrocarbyl-norbornane, α,β,3,3-tetramethyl-bicyclo[2.2.1]heptane-2-propanol having the structure:

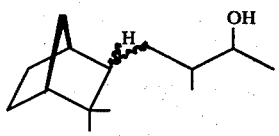

of our invention produced according to Example IC.

Figure 6:
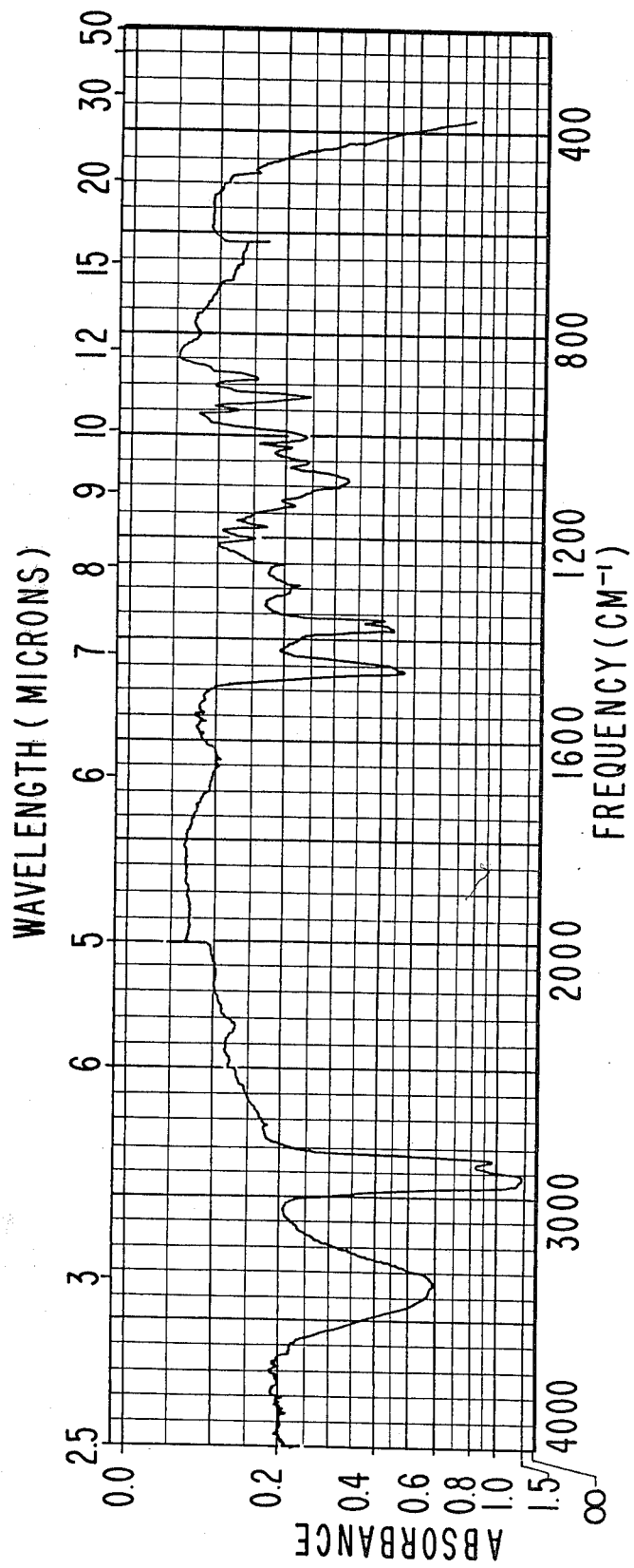

FIG. 6 is the Infrared spectrum for the oxyhydrocarbylnorbornane, α,β,3,3-tetramethyl-bicyclo[2.2.1]heptane-2-propanol having the structure:

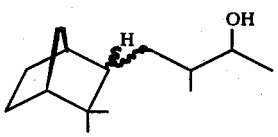

of our invention produced according to Example IC.

THE INVENTION

It has now been discovered that novel perfume compositions, colognes and perfumed articles including soaps, detergents, cosmetics and powders having natural, sweet pine, incense, camphene-like, sweet, green, floral, fruity, dried fruity, ionone-like, orris-like and nasturtium aromas with dried, woody, piney, sweaty and geranic acid-like nuances may be provided by the utilization of one or more of the oxyhydrocarbylnorbornane derivatives having the generic structure:

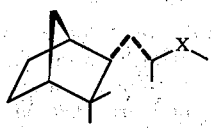

wherein at least one of the dashed lines is a carbon-carbon single bond and the other of the dashed lines is either a carbon-carbon single bond or a carbon-carbon double bond and X is carbonyl or carbinyl having the structures, respectively:

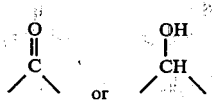

as the "endo" form or the "exo" form or a mixture of "endo" and "exo" forms.

The oxyhydrocarbylnorbornane derivatives of our invention may be produced according to the following reaction sequence:

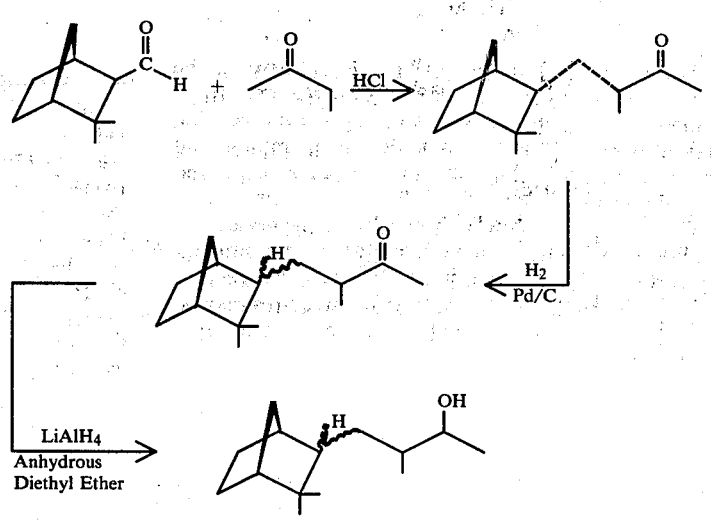

Camphene aldehyde is first reacted with methyl ethyl ketone in the presence of hydrogen chloride. Hydrogen chloride (anhydrous) gas is used to saturate the mixture of methyl ethyl ketone and camphene aldehyde, thereby causing the production of a mixture of compounds (β,3,3-trimethyl-2-norbornyl-α-buten-γ-one and β,3,3-trimethyl-2-norbornylidenebutan-γ-one) having the structures, respectively:

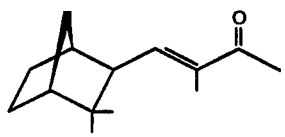

and

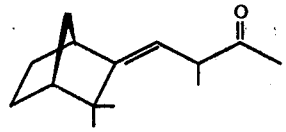

The resulting mixture may, if desired, be used as is for its ability to impart, augment or enhance the aroma of perfume compositions, colognes or perfumed articles, or it may be used as an intermediate in the preparation of other oxyhydrocarbylnorbornane derivatives of our invention. On the other hand, the resulting mixture may be separated using, for example, preparative GLC techniques, thereby producing individually the compound having the structure:

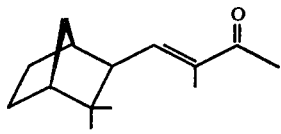

and the compound having the structure:

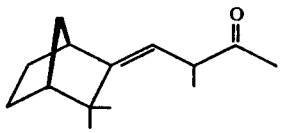

The reaction of the methyl ethyl ketone with the camphene aldehyde preferably takes place at room temperature and atmospheric pressure, but the reaction may also be carried out at higher temperatures and pressures, that is, at pressures up to 5 atmospheres and temperatures up to 50° C.

The resulting mixture may thus be hydrogenated in the presence of a palladium-on-carbon catalyst, preferably at room temperature using a pressure of between 40 and 80 psig. Higher temperatures and pressures may be used if desired but the yield of the reaction product having the structure:

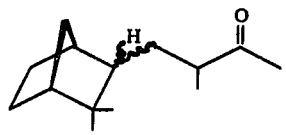

is not effected.

The resulting compound having the structure:

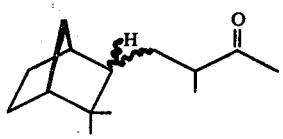

may be used for its properties in augmenting or enhancing the aroma of perfume compositions, perfumed articles and colognes, or it may be used as an intermediate in order to produce the compound having the structure:

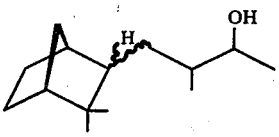

Thus, the compound having the structure:

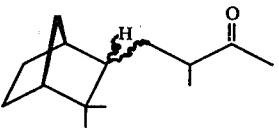

may, if desired, be reduced using a lithium aluminum hydride reducing agent in the presence of an inert solvent, such as anhydrous diethyl ether. The reduction reaction preferably takes place at reflux which is between 35° and 40° C. at atmospheric pressure. The reaction may also take place at higher temperatures and pressures if desired, e.g. 50° C. and 3 atmospheres pressure, but, most conveniently, atmospheric pressure and 35°–40° C. suffices for commercial purposes.

Examples of the oxyhydrocarbylnorbornane derivatives of our invention and their organoleptic properties useful in perfumery are as follows:

| Name of Composition | Structure | Organoleptic Properties |
|---|---|---|
| Mixture of β,3,3-trimethyl-2-norbornyl-α-buten-γ-one and β,3,3-trimethyl-2-norbornylidenebutan-γ-one | | A sweet, floral, dried fruity, ionone-like aroma with a dry, woody, piney nuance. |

-continued

| Name of Composition | Structure | Organoleptic Properties |
| --- | --- | --- |
| 4-(3,3-dimethyl-2-norbornyl)-3-methyl-2-butanone | 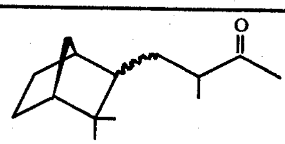 | In 10% food grade ethyl alcohol, a natural, sweet pine, incense-like, camphene-like aroma with a sweaty, geranic acid-like note which remains on dry out. |
| α,β,3,3-tetra-methyl-bicyclo [2.2.1]heptane-2-propanol | 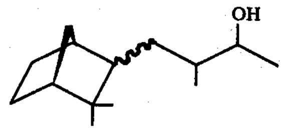 | A green floral, sweet ionone-like, orris-like, nasturtium-like aroma. |

One or more oxyhydrocarbylnorbornane derivatives of our invention and one or more auxiliary perfume ingredients, including for example, other alcohols, aldehydes, nitriles, esters, other ketones, cyclic esters and natural essential oils may be admixed so that the combined odors of the individual components produce a pleasant and desired fragrance particularly and preferably in woody and/or floral and/or piney fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics. However, the over-all sensory effect of the perfume composition will be at least the sum total of the effects of each of the ingredients. Thus, one or more of the oxyhydrocarbylnorbornane derivatives of our invention can be used to alter, modify or enhance the aroma characteristics of a perfume composition, for example, by utilizing or moderating the olfactory reaction contributed by another ingredient in the composition.

The amount of oxyhydrocarbylnorbornane derivatives of our invention which will be effective in perfume compositions as well as in perfumed articles and colognes depends on many factors, including the other ingredients, their amounts and the effects which are desired. It has been found that perfume compositions containing as little as 0.01% of oxyhydrocarbylnorbornane derivatives or even less (e.g., 0.005%) can be used to impart a natural, sweet pine, incense-like, camphene-like, sweet, green, floral, fruity, dried fruity, ionone-like, orris-like and nasturtium-like aroma with dried, woody, piney, sweaty and geranic acid-like nuances to soaps, cosmetics or other products. The amount employed can range up to 70% of the fragrance components and will depend on considerations of cost, nature of the end product, the effect desired on the finished product and the particular fragrance sought.

One or more of the oxyhydrocarbylnorbornane derivatives of our invention are useful [taken alone or together with other ingredients in perfume compositions] as (an) olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of the oxyhydrocarbylnorbornane derivatives of our invention will suffice to impart a natural, sweet pine, incense-like, camphene-like, sweet, green, floral, fruity, dried fruity, ionone-like, orris-like and nasturtium-like aroma with dried, woody, piney, sweaty and geranic acid-like nuances to woody and/or floral and/or piney formulations. Generally, no more than 3% of the oxyhydrocarbylnorbornane derivatives of our invention, based on the ultimate end product, is required in the perfume composition.

In addition, the perfume composition or fragrance composition of our invention can contain a vehicle, or carrier for the oxyhydrocarbylnorbornane derivatives. The vehicle can be a liquid such as a non-toxic alcohol, a non-toxic glycol, or the like. The carrier can also be an absorbent solid, such as a gum (e.g., gum arabic) or components for encapsulating the composition (such as gelatin).

It will thus be apparent that the oxyhydrocarbylnorbornane derivatives of our invention can be utilized to alter, modify or enhance sensory properties, particularly organoleptic properties, such as flavor(s) and/or fragrance(s) of a wide variety of consumable materials.

The following Examples serve to illustrate our invention and this invention is to be considered restricted thereto only as indicated in the appended claims.

All parts and percentages given herein are by weight unless otherwise specified.

EXAMPLE IA

Preparation of mixture of
β,3,3-trimethyl-2-norbornyl-α-buten-γ-one and
β,3,3-trimethyl-2-norbornylidenebutan-γ-one Reaction:

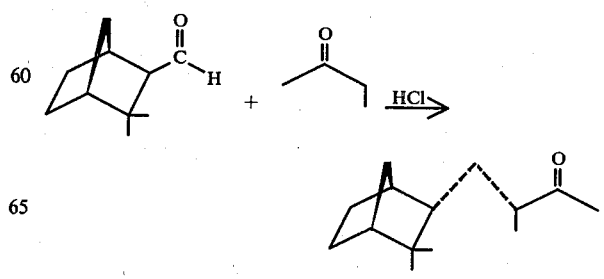

Into a 500 ml reaction flask fitted with a reflux condenser, gas exit scrubber, thermometer, gas tube, gas trap and Primol bubbler are charged 152 grams (1 mole) of camphene aldehyde and 72 grams (1 mole) of methyl ethyl ketone. With stirring, the mixture is saturated with anhydrous hydrogen chloride gas. Hydrogen chloride gas is continued to be bubbled into the reaction mass while maintaining the temperature at 23°–29° C. by means of cooling with an isopropanol dry ice bath. The hydrogen chloride bubbling continues over a period of 4 hours. The reaction mass is continued to be stirred for a period of 4 hours.

The reaction mass is then poured into 200 ml water yielding two phases: an organic phase and an aqueous phase. The aqueous phase is washed with two 200 ml volumes of diethyl ether, and the ether washings are combined with the organic phase. The resulting organic phase is then washed with sodium bicarbonate and water to a pH of 6. The reaction mass is then dried over anhydrous magnesium sulfate; and the diethyl ether, which is in excess, is stripped off. The material is then vacuum distilled (boiling point 90°–100° C.) at 0.6 mm Hg yielding 141 grams of oil. The resulting material is then distilled on a micro Vigreux column after adding thereto 17 grams of Primol ®, yielding the following fractions:

| Fraction No. | Vapor Temperature | Liquid Temperature | Vacuum mm Hg | Weight of Fraction | % Product Contained in Fraction |
|---|---|---|---|---|---|
| 1 | 53–70 | 105–106 | 5.4 | 10.1 | — |
| 2 | 70 | 122 | 2.5 | 2 | — |
| 3 | 103 | 124 | 2.6 | 8 | 50 |
| 4 | 107 | 124 | 2.6 | 11.5 | 67 |
| 5 | 100 | 123 | 2.6 | 8.6 | 76 |
| 6 | 102 | 132 | 2.3 | 11.1 | — |
| 7 | 101 | 137 | 2.3 | 9 | 87 |
| 8 | 74 | 171 | 2.3 | 6.3 | 91 |
| 9 | 100 | 173 | 2.3 | 3 | 41 |

NMR and IR analysis yield the information that the resulting mixture contains two compounds having the structures:

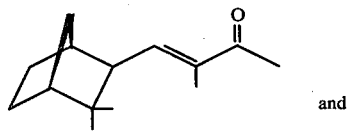

and

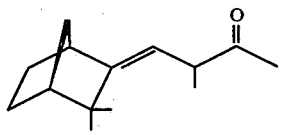

Figure 1:
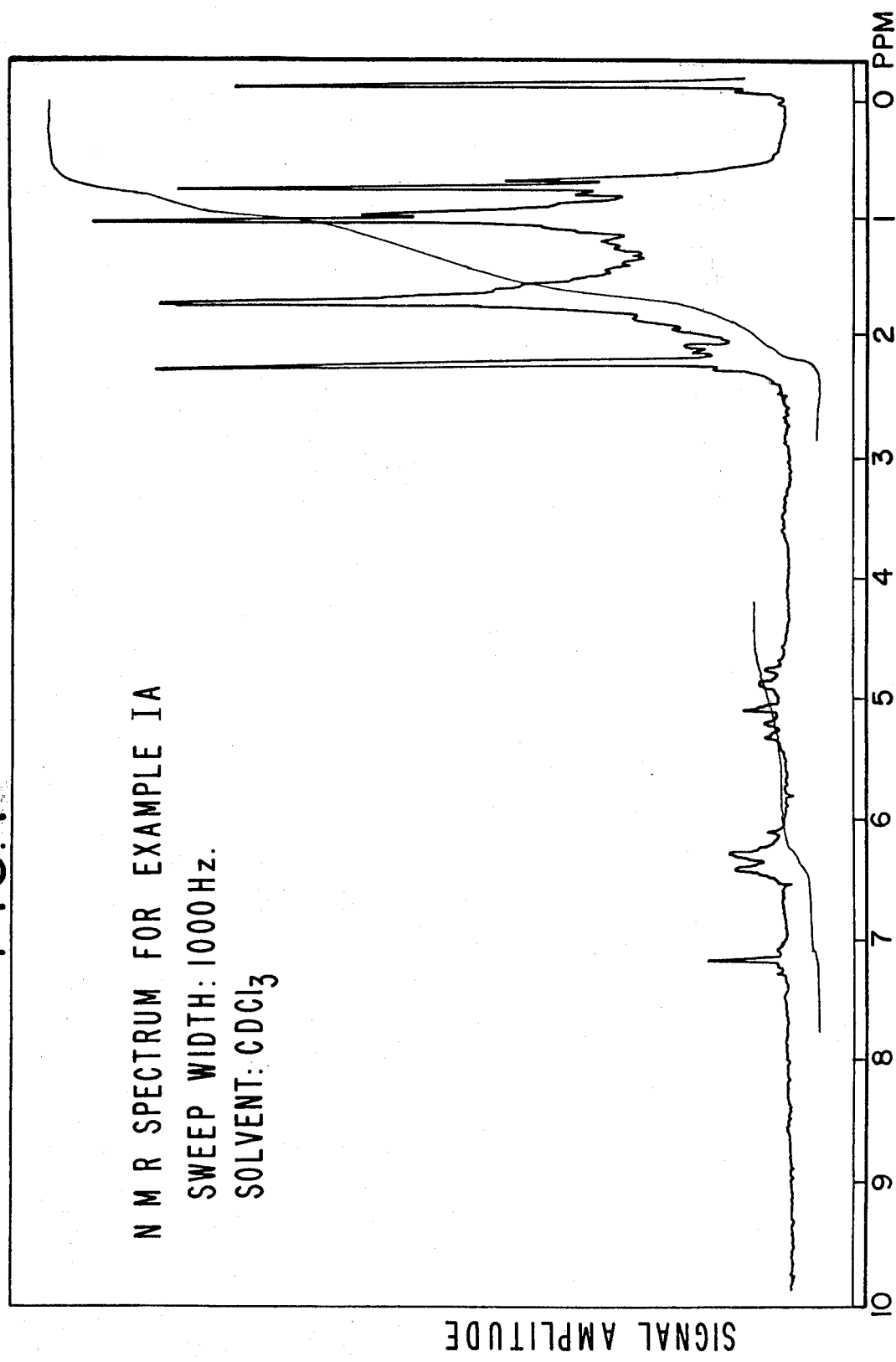
FIG. 1 is the NMR spectrum for the mixture of oxyhydrocarbylnorbornanes, β,3,3-trimethyl-2-norbornyl-α-buten-γ-one and β,3,3-trimethyl-2-norbornylidenebutan-γ-one having the structures respectively.

The NMR spectrum is set forth in FIG. 1 for this mixture. The Infrared spectrum is set forth in FIG. 2.

The Mass Spectrum is as follows:

| m/e | Relative Intensity |
|---|---|
| 39 | 54 |
| 41 | 80 |
| 43 | 100 |
| 53 | 22 |
| 55 | 27 |
| 67 | 28 |
| 79 | 23 |
| 107 | 29 |
| 108 | 22 |

-continued

| m/e | Relative Intensity |
|---|---|
| 109 | 37 |
| M206 | 17 |

EXAMPLE IB

Preparation of 4-(3,3-dimethyl-2-norbornyl)-3-methyl-2-butanone

Reaction:

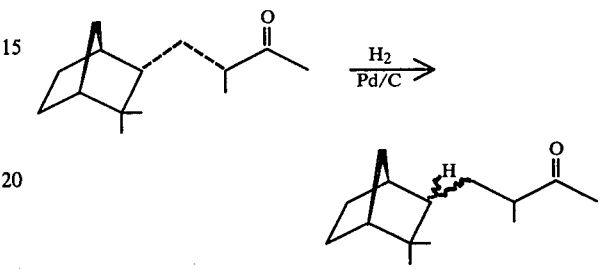

Nine grams of the product produced in Example IA, fraction 9, is admixed with 50 cc of anhydrous isopropyl alcohol and 0.5 grams of a 10% palladium-on-carbon catalyst and the mixture is placed into an autoclave. While maintaining a hydrogen pressure with continuous hydrogen feed at 48–52 psig, the autoclave is shaken for a period of two hours. The autoclave is then opened and the reaction mass is filtered. The resulting reaction mass is dried and solvent stripped to give 8 grams of crude product. The resulting material is micro-distilled, yielding 4 fractions and 0.5 grams of residue. GLC (10% SE-30 column, programmed at 80°–220° C. at 8° C. per minute), NMR and IR analyses yield the information that the resulting product has the structure:

The NMR spectrum is set forth in FIG. 3. The Infrared spectrum is set forth in FIG. 4.

The Mass Spectral analysis is as follows:

| m/e | Relative Intensity |
|---|---|
| 39 | 31 |
| 41 | 54 |
| 43 | 100 |
| 55 | 20 |
| 67 | 22 |
| 69 | 21 |
| 72 | 23 |
| 81 | 18 |
| 93 | 19 |
| 137 | 17 |
| M208 | 11 |

EXAMPLE IC

Preparation of α,β,3,3-tetramethyl-bicyclo[2.2.1]heptane-2-propanol

Reaction:

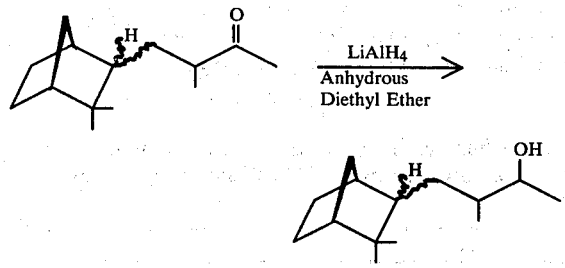

Fraction 2 of the reaction product produced according to Example IB (3 grams) is admixed with 0.5 grams of lithium aluminum hydride and 25 cc of anhydrous diethyl ether in a 50 ml micro-reactor. The reaction mass is refluxed for a period of 1 hour. When the reaction mass no longer exotherms (at the end of the one hour time period) enough water is added to dissolve the salts. The reflux temperature is 37° C.

Water is then added to the reaction mass followed by 2 cc of concentrated hydrochloric acid to dissolve the salts. The reaction mass now exists in two phases; an organic phase and an aqueous phase. The aqueous phase is washed with two volumes of diethyl ether, and the ether extract and organic phases are combined and dried. A major peak is trapped using GLC (10% Carbowax, programmed at 80°–220° C. at 8° C. per minute). NMR, IR and Mass Spectral analyses yield the information that the resulting product has the structure:

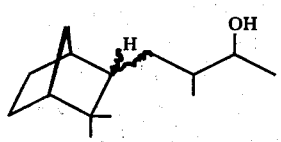

The NMR spectrum is set forth in FIG. 5. The Infrared spectrum is set forth in FIG. 6.

The Mass Spectral analysis is as follows:

| m/e | Relative Intensity |
| --- | --- |
| 39 | 50 |
| 41 | 100 |
| 43 | 60 |
| 45 | 85 |
| 55 | 55 |
| 67 | 58 |
| 69 | 65 |
| 81 | 38 |
| 99 | 70 |
| 109 | 51 |
| M210 | 21 |

EXAMPLE II

PINE NEEDLE FORMULATION

The following formulation is prepared:

| Ingredients | Parts by Weight |
| --- | --- |
| Turpentine gum oil | 100 |
| Limonene | 70 |
| Gum camphor | 10 |
| Isobornyl acetate | 50 |
| Borneol | 30 |
| Mixture of $\beta$,3,3-trimethyl-2-norbornyl-$\alpha$-buten-$\gamma$-one and $\beta$,3,3-trimethyl-2-norbornylidenebutan-$\gamma$-one produced according to Example IA | 40 |
| 4-(3,3-dimethyl-2-norbornyl)-3-methyl-2-butanone produced according to Example IB | 100 |
| $\alpha,\beta$,3,3-tetramethyl-bicyclo[2.2.1]heptane-2-propanol produced according to Example IC | 70 |

The mixture of $\beta$,3,3-trimethyl-2-norbornyl-$\alpha$-buten-$\gamma$-one and $\beta$,3,3-trimethyl-2-norbornylidenebutan-$\gamma$-one produced according to Example IA imparts a sweet, floral, dried fruity, ionone-like aroma with a dry, woody, piney nuance to this pine needle oil formulation.

The 4-(3,3-dimethyl-2-norbornyl)-3-methyl-2-butanone produced according to Example IB imparts a natural, sweet pine, incense-like and camphene-like aroma with a sweaty, geranic acid nuance to this pine needle oil formulation.

The $\alpha$, $\beta$,3,3-tetramethyl-bicycol[2.2.1]heptane-2-propanol produced according to Example IC imparts a green floral, sweet ionone, orris-like and nasturtium aroma to this pine needle oil formulation.

EXAMPLE III

PREPARATION OF A SOAP COMPOSITION

100 Grams of soap chips are mixed with 1 gram of the perfume composition of Example II until a substantially homogeneous composition is obtained. The perfumed soap composition manifests an excellent pine needle fragrance with green floral, sweet ionone, orris-like, nasturtium-like, sweet pine, incense and camphene-like notes and sweaty, geranic acid nuances which remain on dry out.

EXAMPLE IV

PREPARATION OF A COSMETIC POWDER COMPOSITION

A cosmetic powder is prepared by mixing in a ball mill, 100 g of talcum powder with 0.25 g of the composition prepared according to Example II. It has an excellent pine needle aroma with green floral, sweet ionone, orris-like, nasturtium-like, sweet pine, incense and camphene-like notes and sweaty, geranic acid nuances which remain on dry out.

EXAMPLE V

PERFUMED LIQUID DETERGENT

Concentrated liquid detergents (lysine salt of n-dodecyl benzene sulfonic acid as more specifically described in U.S. Pat. No. 3,948,818, issued on Apr. 6, 1976) with intense pine needle aromas are prepared containing 0.10%, 0.15% and 0.20% of the perfume composition produced according to Example II. The detergents are prepared by adding and homogeneously mixing the appropriate quantity of perfume oil composition of Example II. The detergents all possess intense pine needle aromas, with green floral, sweet ionone, orris-like, nasturtium-like, sweet pine, incense and camphene-like notes, with the intensity increasing with greater concentrations of the formulation of Example II.

EXAMPLE VI

PREPARATION OF A COLOGNE AND HANDKERCHIEF PERFUME

The composition produced according to Example II is incorporated into a cologne at a concentration of 2.5% in 85% aqueous ethanol. A distinct and definite pine needle fragrance with green floral, sweet ionone, orris-like, nasturtium-like, sweet pine, incense and camphene-like notes is imparted to the cologne. The composition of Example II is also added to a handkerchief perfume at a concentration of 20% (in 95% aqueous ethanol) and a distinct and definite pine needle fragrance with green floral, sweet ionone, orris-like, nasturtium-like, sweet pine, incense and camphene-like notes is imparted to the handkerchief perfume.

EXAMPLE VII

PREPARATION OF A SOAP COMPOSITION

100 Grams of soap chips are mixed with 1 gram of the perfume composition of 4-(3,3-dimethyl-2-norbornyl)-3-methyl-2-butanone prepared according to Example IB until a substantially homogeneous composition is obtained. The perfumed soap composition manifests an excellent natural sweet pine aroma with incense and camphene-like notes and sweaty, geranic acid nuances.

EXAMPLE VIII

PREPARATION OF A SOAP COMPOSITION

100 Grams of soap chips are mixed with 1 gram of α,β,3,3-tetramethyl-bicyclo[2.2.1]heptane-2-propanol prepared according to Example IC. The perfumed soap composition manifests an excellent green floral, sweet ionone, orris-like and nasturtium characteristic.

EXAMPLE IX

A perfume composition is prepared by admixing the following ingredients in the indicated proportions:

| Ingredient | Amount (Grams) |
|---|---|
| n-Decyl Aldehyde | 1 |
| n-Dodecyl Aldehyde | 2 |
| Methyl Nonyl Acetaldehyde | 0.5 |
| Linalool | 50 |
| Linalyl Acetate | 70 |
| Phenyl Ethyl Alcohol | 100 |
| Petigrain SA | 20 |
| Bergamot Oil | 30 |
| Alpha Methyl Ionone | 25 |
| 4-(3,3-dimethyl-2-norbornyl)-3-methyl-2-butanone produced according to Example IB | 10 |
| Cyclized Bicyclo C-12 material produced according to the process of Example IV of Canadian Patent 854,225, issued on October 20, 1970 | 5 |
| Isobornyl cyclohexyl alcohol | 10 |
| Benzyl Acetate | 25 |
| 2-n-Heptyl cyclopentanone | 5 |
| | 353.3 (TOTAL) |

The foregoing blend is evaluated and found to have a high degree of richness and persistence in its novel natural, sweet piney, incense-like and camphene-like character. This base composition can be admixed with aqueous ethanol, chilled and filtered to produce a finished cologne. The cologne so prepared has a natural, sweet pine, incense and camphene-like aroma with a sweaty, geranic acid note which remains on dry out. This note is quite desirable and valuable. The base composition can also be used to scent soap or other toilet goods such as lotions, aerosols, sprays and the like.

EXAMPLE X

A perfume composition is prepared by admixing the following ingredients in the indicated proportions:

| Ingredient | Amount (Grams) |
|---|---|
| n-Decyl Aldehyde | 1 |
| n-Dodecyl Aldehyde | 2 |
| Methyl Nonyl Acetaldehyde | 0.5 |
| Linalool | 50 |
| Linalyl Acetate | 70 |
| Phenyl Ethyl Alcohol | 100 |
| Petigrain SA | 20 |
| Bergamont Oil | 30 |
| Alpha Methyl Ionone | 25 |

The foregoing blend is evaluated and found to have a high degree of richness and persistence in its novel green floral, sweet ionone-like, orris-like and nasturtium-like quality. This base composition can be admixed with aqueous ethanol, chilled and filtered to produce a finished cologne. The cologne so prepared has a green floral, sweet ionone-like, orris-like and nasturtium-like aroma. The base composition can also be used to scent soap or other toilet goods such as lotions, aerosols, sprays and the like.

EXAMPLE XI

PREPARATION OF A COSMETIC POWDER COMPOSITION

A cosmetic powder is prepared by mixing in a ball mill 100 g of talcum powder with 0.25 g of α,β,3,3-tetramethyl-bicyclo[2.2.1]heptane-2-propanol prepared according to Example IC. It has an excellent green floral, sweet ionone-like, orris-like and nasturtium-like aroma.

What is claimed is:

1. A process for preparing a solid or liquid anionic, cationic or nonionic detergent comprising the step of combining with a solid or liquid nonionic, anionic or cationic detergent base from 0.1% up to 1% by weight of at least one oxyhydrocarbylnorbornane derivative having the structure:

wherein X is carbonyl or carbinyl having the structures, respectively:

$$\underset{C}{\overset{O}{\|}} \quad \text{or} \quad \underset{CH}{\overset{OH}{|}}$$

and wherein at least one of the dashed lines is a carbon-carbon single bond and the other of the dashed lines is a carbon-carbon single bond or a carbon-carbon double bond.

2. The process of claim 1 wherein the detergent is a soap.

3. The process of claim 1 wherein the oxyhydrocarbylnorbornane is a mixture having the structures:

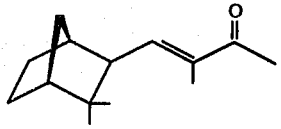

and

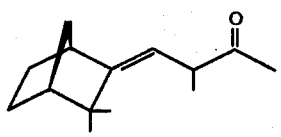

4. The process of claim 1 wherein the oxyhydrocarbylnorbornane has the structure:

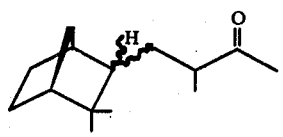

wherein the wavy lines represent C—H and C—C single bonds in a "cis" and "trans" configuration with respect to the norbornyl moiety.

5. The process of claim 1 wherein the range of oxyhydrocarbylnorbornane derivative added to the detergent base is from 0.1% up to 0.2%.

* * * * *